United States Patent [19]

Steinke et al.

[11] Patent Number: 5,328,472
[45] Date of Patent: Jul. 12, 1994

[54] CATHETER WITH FLEXIBLE SIDE PORT ENTRY

[75] Inventors: Thomas A. Steinke, San Diego; Leonard F. Briggs, Chula Vista; Garry E. Rupp, San Diego, all of Calif.

[73] Assignee: Medtronic, Inc., Minneapolis, Minn.

[21] Appl. No.: 919,672

[22] Filed: Jul. 27, 1992

[51] Int. Cl.⁵ .......................................... A61M 29/00
[52] U.S. Cl. ................................... 604/102; 604/96; 604/282; 606/194
[58] Field of Search ............ 604/96, 102, 280, 282; 128/656–658, 772; 606/191, 192, 194

[56] References Cited

U.S. PATENT DOCUMENTS

| | | | |
|---|---|---|---|
| 4,594,074 | 6/1986 | Anderson et al. | 604/270 |
| 4,648,384 | 3/1987 | Schmukler | 128/1 |
| 4,723,936 | 2/1988 | Buchbinder et al. | 604/95 |
| 4,748,982 | 6/1988 | Horzewski et al. | 128/344 |
| 4,762,129 | 8/1988 | Bonzel | 128/344 |
| 4,771,777 | 9/1988 | Horzewski et al. | 128/344 |
| 4,790,315 | 12/1988 | Mueller, Jr. et al. | 128/344 |
| 4,804,358 | 2/1989 | Karcher et al. | 600/17 |
| 4,832,028 | 5/1989 | Patel | 128/344 |
| 4,838,268 | 6/1989 | Keith et al. | 128/344 |
| 4,877,031 | 10/1989 | Conway et al. | 128/344 |
| 4,892,519 | 1/1990 | Songer et al. | 604/96 |
| 4,909,252 | 3/1990 | Goldberger | 606/194 |
| 4,917,666 | 4/1990 | Solar et al. | 604/95 |
| 4,927,413 | 5/1990 | Hess | 604/95 |
| 4,943,278 | 7/1990 | Euteneuer et al. | 604/96 |
| 4,944,740 | 7/1990 | Buchbinder et al. | 606/194 |
| 4,944,745 | 7/1990 | Sogard et al. | 606/194 |
| 4,976,689 | 12/1990 | Buchbinder et al. | 604/95 |
| 4,988,356 | 1/1991 | Crittenden et al. | 606/192 |
| 5,000,753 | 3/1991 | Hagen et al. | 606/32 |
| 5,040,548 | 8/1991 | Yock | 128/898 |
| 5,061,273 | 10/1991 | Yock | 606/194 |
| 5,125,895 | 6/1992 | Buchbinder et al. | 604/95 |
| 5,154,725 | 10/1992 | Leopold | 606/194 |
| 5,156,594 | 10/1992 | Keith | 604/96 |

FOREIGN PATENT DOCUMENTS

| | | | |
|---|---|---|---|
| 0420486 | 3/1991 | European Pat. Off. | A61M 29/02 |
| 8803389 | 5/1988 | PCT Int'l Appl. | A61B 10/00 |
| 9108013 | 6/1991 | PCT Int'l Appl. | A61M 25/10 |

Primary Examiner—C. Fred Rosenbaum
Assistant Examiner—Corrine Maglione
Attorney, Agent, or Firm—Dianne M. F. Plunkett; Harold R. Patton

[57] ABSTRACT

An improved balloon catheter is disclosed which is comprised of two jacketed spring coils placed end-to-end and joined by a linking element which contains a lumen communicating between the inflation lumens formed by the two spring coils. A side port entry to a guidewire lumen, which extends through the distal coil to the distal end of the catheter, is located in the transition region formed by the linking element. The linking element may include two polyimide tubes or may be a multilumen insert. The catheter is stiffened by a core wire which is bonded directly to the spring coils. A catheter comprised of a single spring coil with a side port entry in the coil is also disclosed, and a method and apparatus for crimping the coil to create the entry.

12 Claims, 7 Drawing Sheets

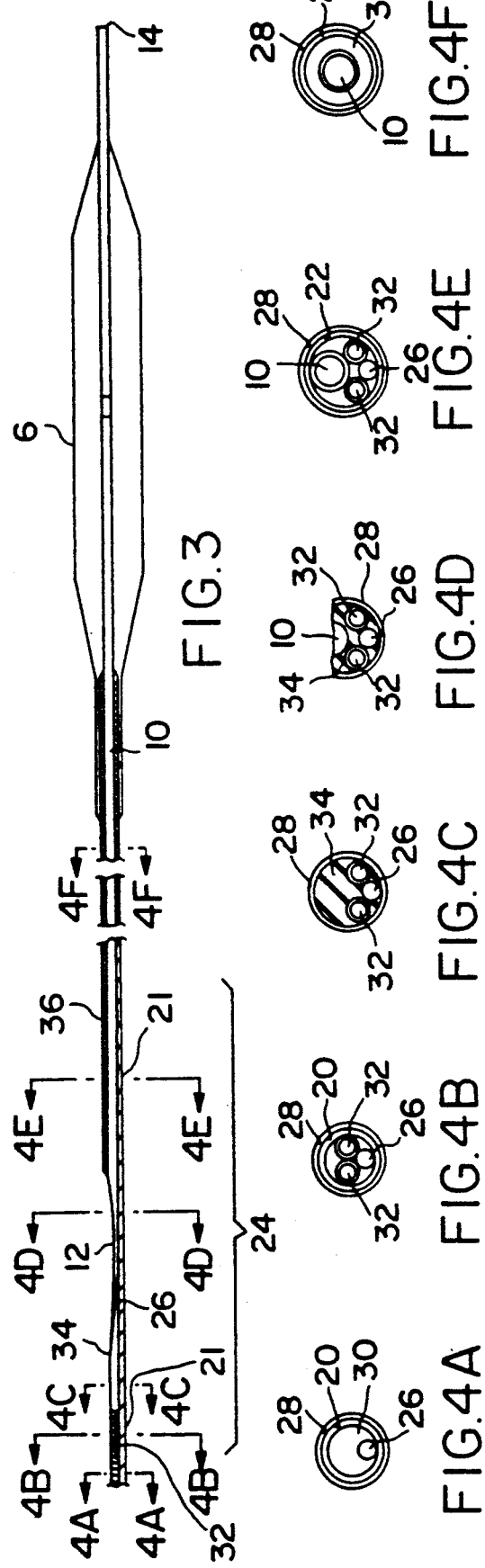

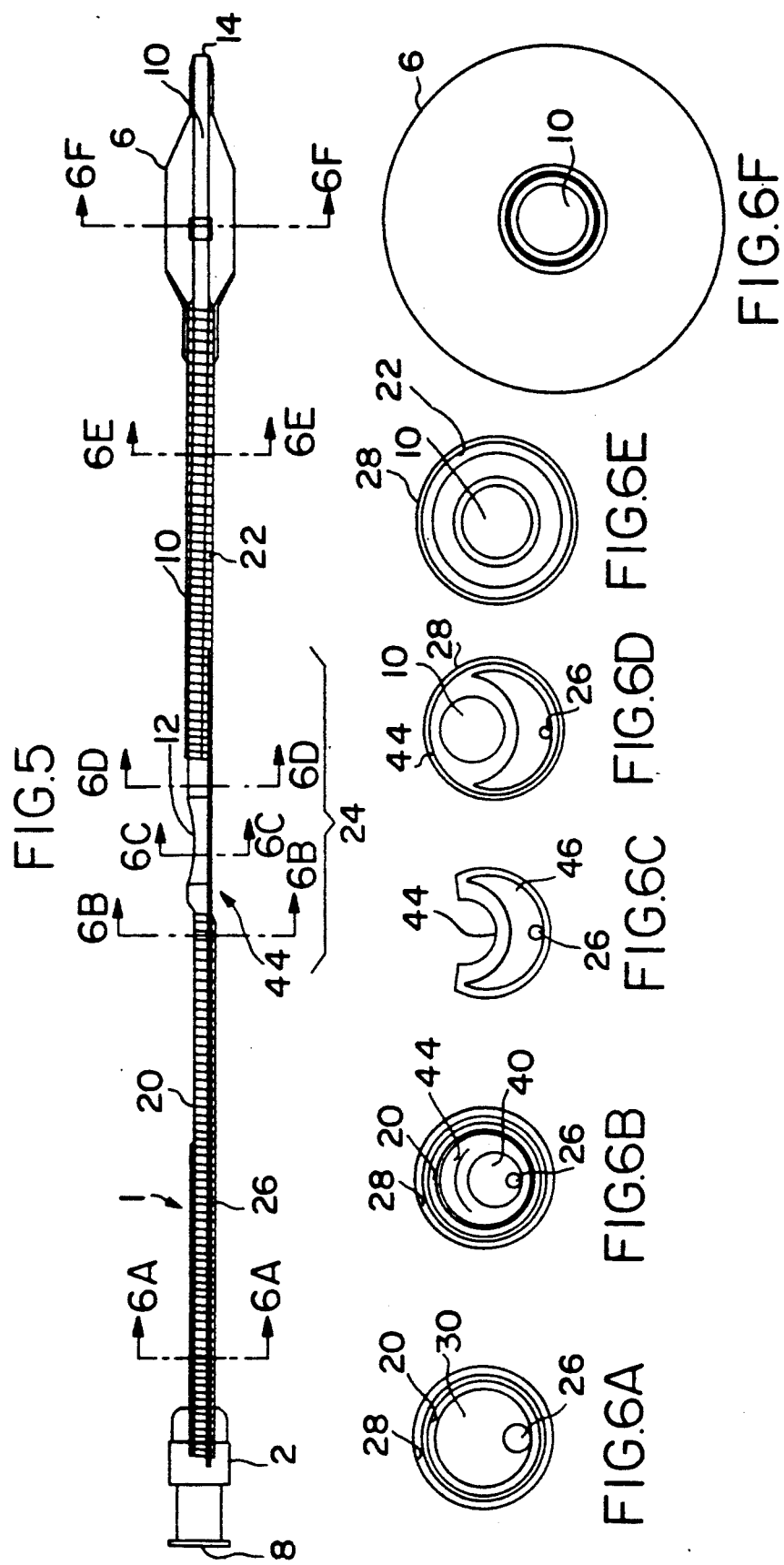

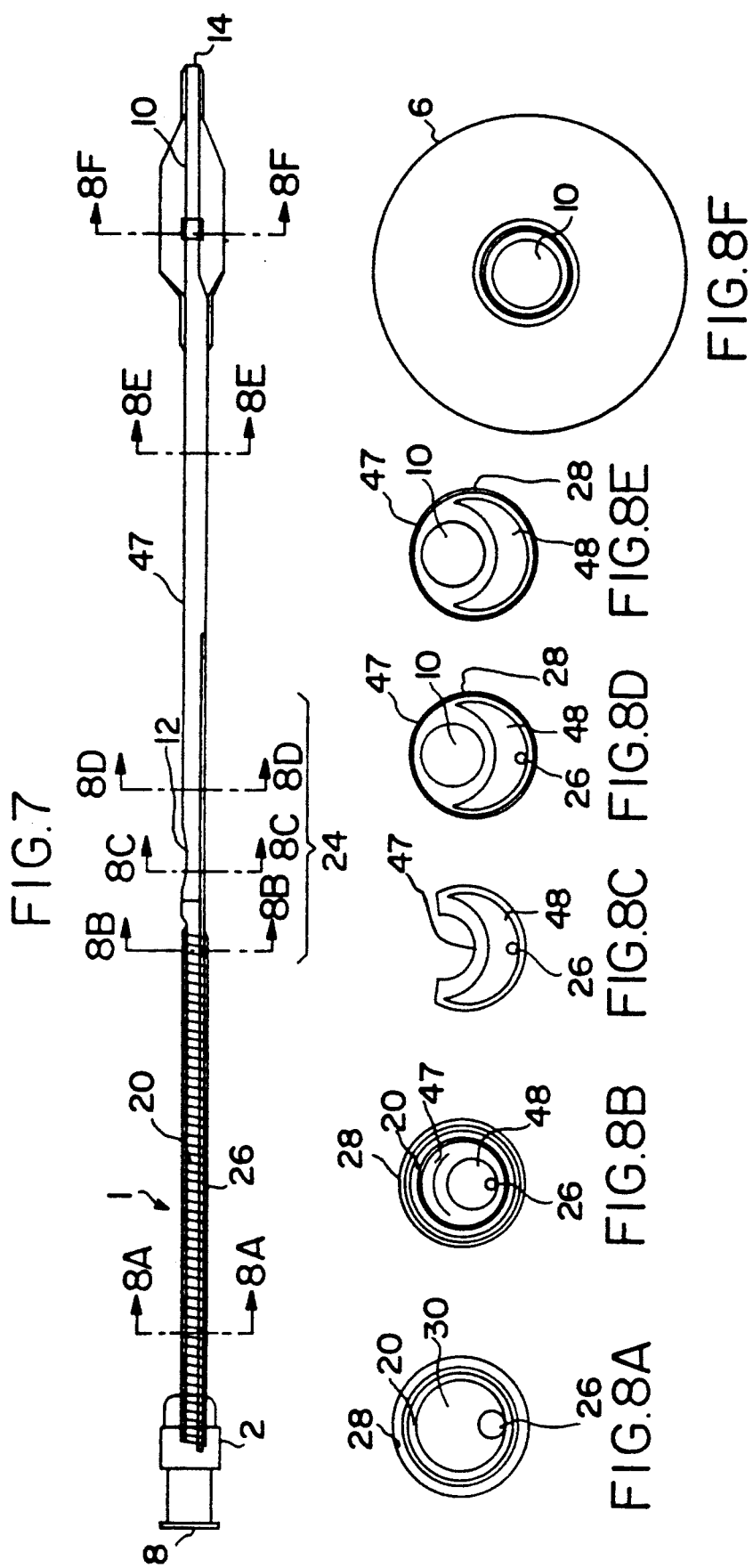

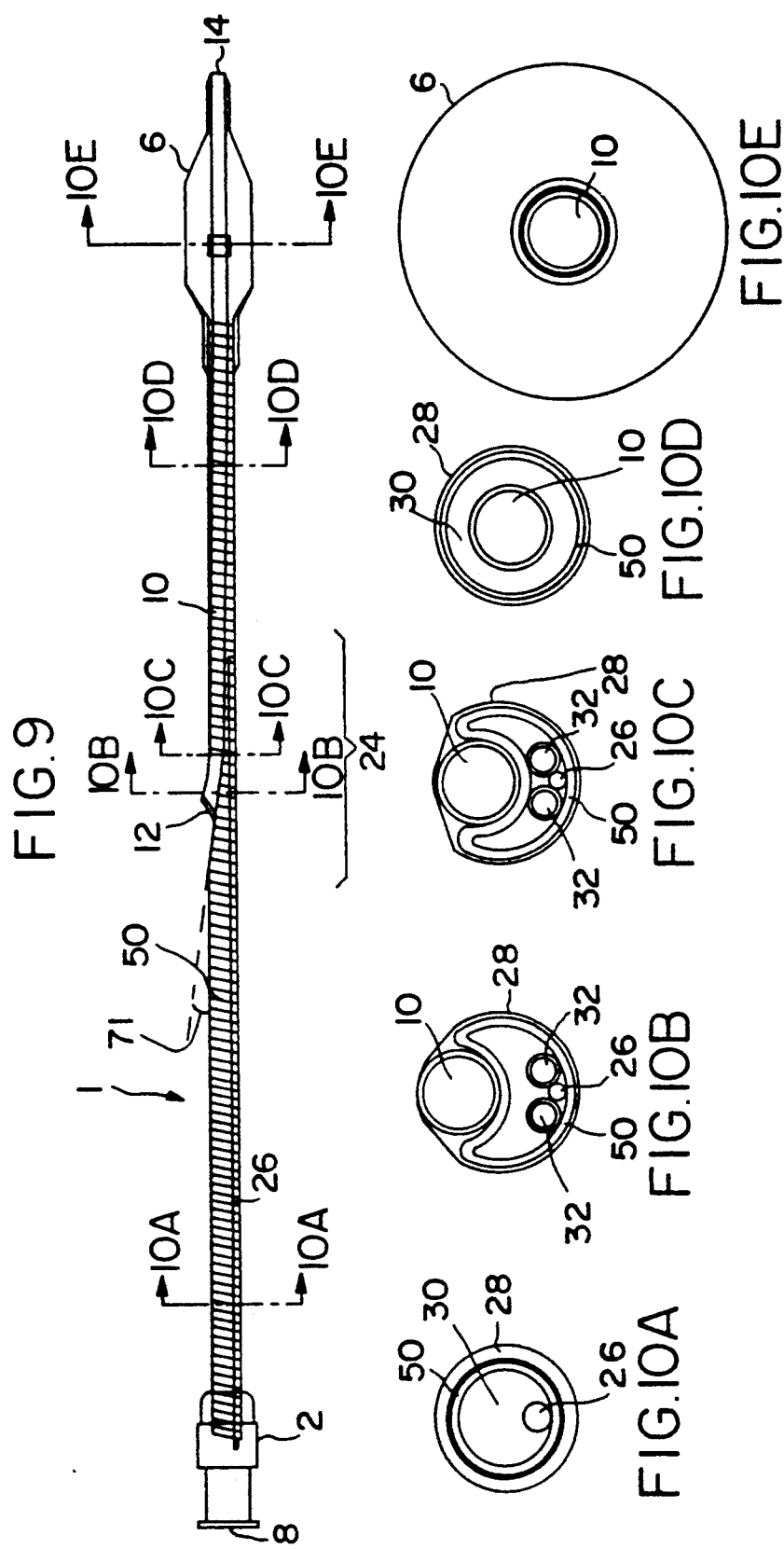

CATHETER WITH FLEXIBLE SIDE PORT ENTRY

BACKGROUND OF THE INVENTION

The technique of eliminating a vascular stenosis by dilating a balloon on a catheter placed within the stenosis was developed by Dr. Andreas Gruntzig. The first marketable catheters for angioplasty were "fixed wire" catheters, in which a core or guidewire was fixed within the catheter to stiffen it so that it could be pushed into position in the vascular system.

Dr. John Simpson and Dr. Edward Robert subsequently developed an "over-the-wire" catheter in which a guidewire was slidably placed within a lumen of the catheter. This system provided reasonably easy placement of the catheter because the guidewire was first positioned beyond the stenosis and the catheter was then slid into place over it. Although over-the-wire catheters generally have a larger profile than fixed wire catheters, the guidewire can be much more easily positioned in the vascular system than a fixed wire catheter.

Both over-the-wire and fixed wire catheters are usually made using polymer tubing to form the catheter body. In some catheters, however, the catheter shaft is formed of a spring coil (a helically wound wire) jacketed on the outside or inside so that it is sealed to form a lumen. For example, U.S. Pat. Nos. 4,976,689, 4,944,740, 4,917,666 and 4,723,936 issued to the assignee of the present invention describe such catheters. Although more expensive and more complicated to make than polymer catheters, spring coil catheters have certain advantages. They allow flexibility in the catheter while providing greater axial stiffness than a typical polymer extrusion. As a result, the catheter is very "pushable", i.e., axial force at one end is transmitted to the other end. In addition, kinking of the catheter as it bends around curves is minimized. The use of flat wire rather than round wire is preferred because it has greater resistance to compression and less tendency to deform.

An advantage of over-the-wire catheters is that if a catheter has to be exchanged for a larger or smaller catheter, the guidewire can be left in place and the catheter withdrawn over it and another catheter slid into place over it. A difficulty with the exchange procedure is that it is difficult to keep the guidewire in place, because removing the catheter requires removal of the guidewire and subsequent recrossing of the stenosis. To avoid this problem, very long "exchange" guidewires, more than twice the length of the catheter, are used so that they can be separately held in place while the catheter is withdrawn. In addition, shorter guidewires have been made, which are lengthened by attachment of an extension wire during the exchange process in order to render them the length of a long exchange wire. Unfortunately, such long guidewires and extension wires require an additional person to hold the guidewire during the catheterization process and are somewhat difficult to use.

This problem was solved by the development of catheters which have shorter guidewire lumens, so that the guidewire exits from the catheter closer to the balloon than to the proximal end of the catheter. Thus the guidewire can be anchored or held by the physician as he or she removes the catheter from the body and the exchange occurring over the shorter guidewire lumen.

One version of such a catheter is shown in U.S. Pat. No. 4,762,129 (and B1 4,762,129) issued to Bonzel, where the guidewire lumen passes through the balloon and exits immediately proximal to the balloon. The guidewire lumen and inflation lumen are of a "bilumen" or "biaxial" configuration in which the guidewire lumen runs parallel to the inflation lumen. A similar system is shown in U.S. Pat. No. 4,748,982 issued to Horzewski, et al., and in U.S. Pat. No. 4,988,356 issued to Crittenden, in which the guidewire lumen, which runs parallel to the inflation lumen, contains a slit extending its length so that the guidewire can be removed from the lumen through the slit at a point immediately proximal to the balloon.

These bilumen designs can be relatively easy to manufacture because they can be made from a single extrusion of the shaft and guidewire lumen together. In addition, they allow use of a slit guidewire lumen. Sometimes, however, they have a larger profile than might be desired and poor guidewire movement.

Examples of bilumen rapid exchange catheters on the market are ACS' Alpha TM catheter and ACS' RX TM catheter. In the Alpha TM catheter, a hypotube (stainless steel tube) forms the proximal end of the catheter and a bilumen extrusion the distal portion. The bilumen portion is slit so that the guidewire can be removed from it at varying positions as shown in the Horzewski, et al., patent mentioned above. In the RX TM catheter, the entire catheter is a single bilumen extrusion, the proximal portion of which contains a core wire. A side entry is cut into the guidewire lumen near the balloon.

In rapid exchange catheter designs such as those in Yock, U.S. Pat. Nos. 5,040,548 and 5,061,273, the short guidewire lumen is coaxial with respect to the inflation lumen, but exits (or enters) in a side port at least 10 centimeters from the distal tip of the catheter. (The Yock disclosure suggests a lumen of 10 or more centimeters; in catheters on the market, the coaxial lumen varies from about 9 to about 35 centimeters in length.) Coaxial construction has provided certain advantages such as smaller profile catheters and better guidwire movement.

However, in these catheters, the construction of the distal guidewire entry area or "transition region" has posed a challenge. The inflation lumen must be isolated from the distal port to prevent exit of the inflation fluid to the exterior. In some designs, the transition region is not strong enough to avoid distal kinking. In others, abrupt changes in stiffness from one part of the catheter to another may occur. In yet others, the transition region may be too stiff, preventing its placement in the coronary arteries.

An example of a coaxial rapid exchange catheter on the market is Schneider's Piccolino TM. In this catheter, the entire inflation lumen appears to be formed of one piece, and a core wire extends through the proximal portion, through the transition region and into the distal portion. The guidewire lumen is located in the distal end of the inflation lumen and appears to be fused into position in the transition area. An entry is cut into the proximal end of the guidewire and adjacent fused area.

In SciMed's Express TM catheter, a hypotube forms the proximal segment and a separate hypotube segment formed into a crescent shape is attached to the distal end of the proximal hypotube, creating a trough in which the guidewire lumen is located. A short coil jacketed by the inflation lumen surrounds the guidewire lumen, reinforcing the transition. The remaining distal segment of the catheter is made of standard coaxial extrusions.

It would be desirable to develop a catheter which allows rapid exchange, has the benefits of a coaxial guidwire lumen, has the advantages of a spring coil design, and which can be designed for appropriate but varying flexibility along the length of the catheter, without abrupt changes in stiffness, or an undesirably stiff transition region.

SUMMARY OF THE INVENTION

The present invention is directed to an improved catheter and method of making and using same which can be manufactured with variable stiffness characteristics, appropriate flexibility, and desired amounts of axial stiffness.

In one aspect, the invention is a method of making a catheter including the following steps:
  selecting two tubular members for the catheter body, each defining a lumen;
  placing the tubular members end-to-end;
  spacing the ends of the tubular members from each other to create a transition region therebetween; and
  providing a linking element in the transition region defining a lumen to communicate between the lumens of the two tubular members, so that by varying the characteristics of the tubular members and the linking element, the handling characteristics of the catheter can be controlled.

In another aspect, the invention is a catheter body comprised of two tubular members having lumens placed end-to-end and spaced apart by a linking element having a lumen communicating between the lumens of the two tubular members. Generally, the method also includes the steps of providing a side port entry in the transition region and a third tubular member within the distal tubular member to act as a guidewire lumen. The catheter also preferably includes such a third tubular member. The first two tubular members are preferably formed of spring coils and the linking element is a flexible tube, sometimes two flexible tubes, usually formed of polyimide. Sometimes the linking element is a single multilumen element comprising both the guidewire lumen and a lumen communicating between the inflation lumens of the spring coils.

In another aspect, the invention is a catheter having a spring coil shaft defining a lumen and a side port and having a distal and proximal end. The catheter preferably includes a balloon located generally at the distal end of the shaft, the balloon having a distal and a proximal end, and a lumen extending from the distal end to the side port, the lumen adapted to receive a guidewire in a sliding fit. The distal end of the balloon is sealed to the lumen and the proximal end of the balloon is sealed to the shaft. The shaft is usually jacketed with polyethylene and a core wire is bonded to the shaft to stiffen the catheter. Preferably the spring coil shaft is formed of two spring coils placed end-to-end to define a transition region therebetween; the side port entry located in the transition region, as described in more detail above. Alternately, the entry may be located in a single spring coil shaft, and one or more flexible tubes, preferably polyimide, sealed adjacent the entry to communicate between the distal and proximal ends of the coil.

In another aspect, the invention is a method of using a catheter including the following steps:
  providing a catheter including a spring coil shaft defining a lumen and a side port and having a distal and proximal end, a lumen extending from the distal end to the side port, said lumen adapted to receive a guidewire in a sliding fit and a treatment region located at the distal end of the shaft;
  providing a guiding catheter;
  providing a guidewire;
  inserting the guiding catheter into a vascular system having a stenosis;
  threading the guidewire through the vascular system and through the stenosis;
  threading the catheter over the guidewire to locate the treatment means with respect to the stenosis; and
  withdrawing the catheter.

Preferably, the method also includes the following steps:
  providing a second catheter including a spring coil shaft defining a lumen and a side port and having a distal and proximal end, a lumen extending from the distal end to the side port, said lumen adapted to receive a guidewire in a sliding fit and a treatment region located at the distal end of the shaft;
  inserting the second catheter over the guidewire;
  treating the stenosis; and
  withdrawing the second catheter.

Generally, the treatment means of the catheter is a dilatation balloon having a distal end sealed to the lumen and a proximal end sealed to the shaft, and the step of treating the stenosis includes inflating the balloon to dilate the stenosis. The spring coil shaft of the catheter is preferably formed of two spring coils located end-to-end and defining a transition region therebetween; the side port located in the transition region, and the catheter most preferably has one or more of the additional features already described above.

In another aspect, the invention is a catheter including an elongated shaft defining a lumen and a core wire for stiffening the shaft, where the core wire is bonded directly to the shaft. Preferably the shaft is a spring coil and the core wire is brazed to it. Most preferably, the shaft is comprised of two spring coils spaced end-to-end and the core wire is fixed to both spring coils, and the catheter has one or more of the additional features already mentioned.

In another aspect, the invention is a method of creating a side entry along the length of the shaft of a catheter having the following steps:
  providing a spring coil shaft;
  connecting the coils together in an area of the shaft;
  crimping some of the connected coils sufficiently to create an entrance to the shaft while maintaining a lumen through the crimped coils.

The step of connecting the coils generally includes brazing the coils to render them more shapable and may include welding them to a core wire extending through the coil. One or more core wires may be inserted through the coils to be crimped to maintain a lumen through the crimped coils. The core wire is usually 0.014" in diameter and may be a hypotube mandrel shaped in a "U" or crescent. One or more flexible shafts may be inserted into the lumen to carry the inflation fluid. A guidewire lumen is usually inserted in the distal portion of the coils and opens to the exterior of the catheter at the side port entry.

In yet another aspect, the invention is apparatus for creating a side port entry in a spring coil shaft including means for retaining the spring coil in a fixed position, means for crimping a length of spring coil, and means for adjusting the crimping means between crimping and non-crimping position.

The means for retaining the spring coil in a fixed position are usually two blocks forming a space therebetween for holding the spring coil. The crimping means is a tongue having a lower edge extending lengthwise with respect to the coil. The two blocks are movable relative to each other, via an arm attached to an eccentric cam, so that coils of different sizes can be accommodated. The tongue can be variably positioned with respect to the spring coil via an arm attached to an eccentric cam. The tongue is removable and tapered lengthwise to provide a desired entry angle (of about 6 degrees) for the side port entry.

Other aspects and advantages of the invention will be apparent to those of ordinary skill in the art.

BRIEF DESCRIPTION OF THE DRAWINGS

FIG. 3 is a cross-section, taken lengthwise, of the preferred catheter of the present invention, taken lengthwise, showing the balloon, the transition zone, and the side port entry.

FIGS. 4A, 4B, 4C, and 4D, 4E, and 4F are cross-sections of the catheter taken at lines 4A, 4B, 4C, 4D, 4E, and 4F, of FIG. 3, respectively.

FIG. 5 is a cross-section of the transition region and adjacent shaft, taken lengthwise, of another embodiment of the present invention.

FIGS. 6A, 6B, 6C, 6D, 6E and 6F are cross-sections of the transition region and shaft of the present invention taken at lines 6A, 6B, 6C, 6D, 6E and 6F of FIG. 5.

FIG. 7 is a cross-section of the transition region and adjacent shaft, taken lengthwise, of another embodiment of the present invention.

FIGS. 8A, 8B, 8C, 8D, 8E and 8F are cross-sections of the transition region and shaft, taken at lines 8A, 8B, 8C, 8D, 8E and 8F, respectively, of FIG. 7.

FIG. 9 is a cross section of the transition region and adjacent shaft, taken lengthwise, of another embodiment of the present invention.

FIGS. 10A, 10B, 10C, 10D, and 10E are cross-sections of the transition region and shaft, taken at lines 10A, 10B, 10C, 10D, and 10E of FIG. 9, respectively.

DETAILED DESCRIPTION OF THE SPECIFIC EMBODIMENTS

Figure 1:
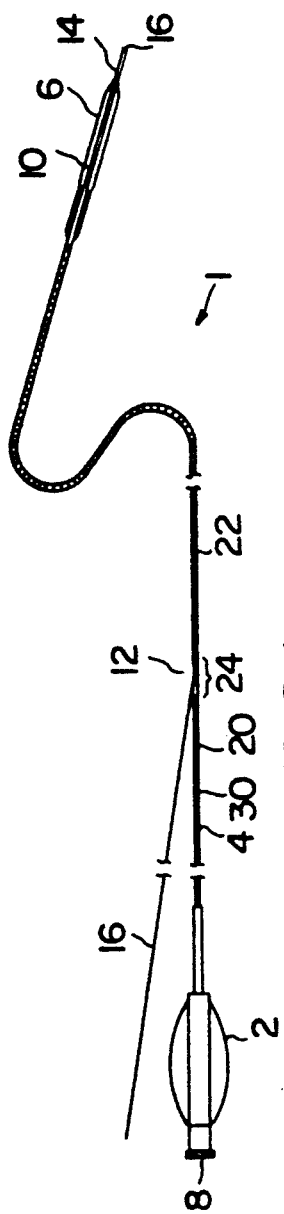
FIG. 1 is a perspective view of the preferred embodiment of the catheter of the present invention.

An angioplasty catheter 1 of the present invention is shown schematically in FIG. 1. It includes an adapter 2, a catheter body 4 defining an inflation lumen 30, and a balloon 6 disposed at the distal end of the catheter body. The balloon is inflated by fluid passing through the inflation lumen from the proximal end 8 of the catheter into the balloon. An inner lumen 10 located within the catheter body extends through the balloon, and the distal end of the balloon is sealed to the inner lumen near the distal end of the lumen.

The inner lumen exits to the exterior of the catheter through a side port entry 12 distal to the proximal end of the catheter 8, but proximal to the balloon. Preferably the side port entry is located about 20 centimeters from the distal tip 14 of the catheter. A guidewire 16 can be slidingly received within the inner lumen. The length of the balloon will vary but, in the preferred embodiment, it is about 20 mm long and blow-molded from a polyethylene tube in a manner known to those in the art.

Figure 2:
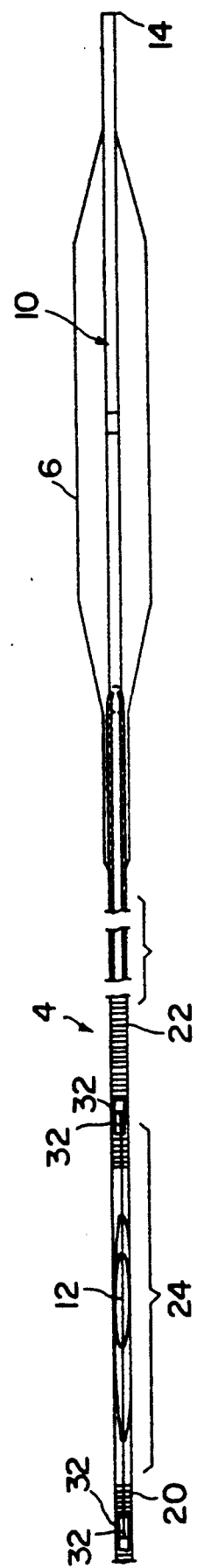
FIG. 2 is a top plan view, partially cut away, of the preferred catheter of the present invention, showing the transition zone and side port entry.
Figure 11:
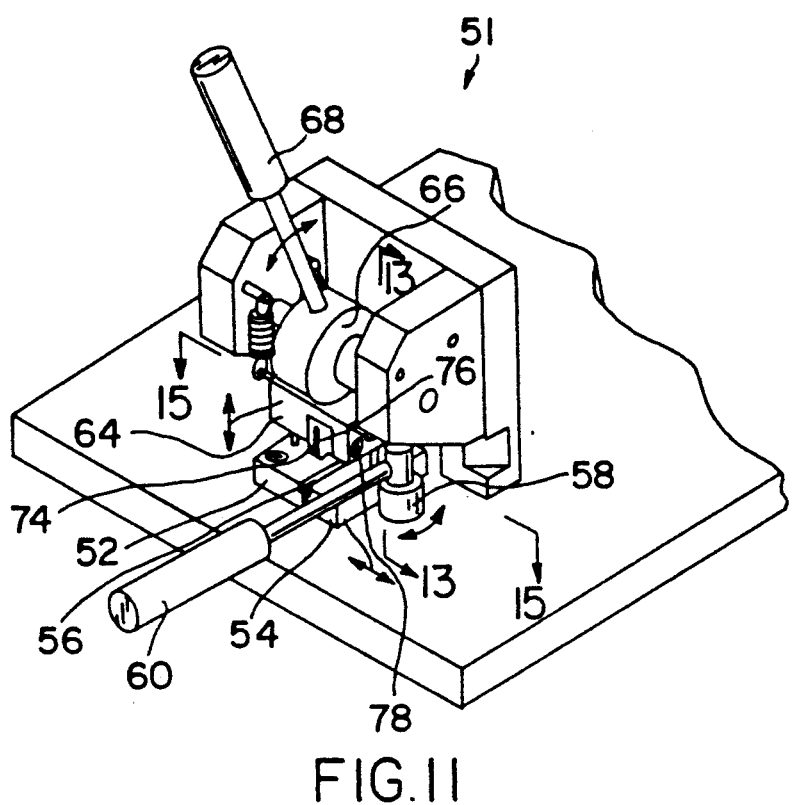
FIG. 11 is a side elevation of apparatus used to create the side port entry in the transition region of the embodiment of the present catheter shown in FIG. 9.
Figure 12:
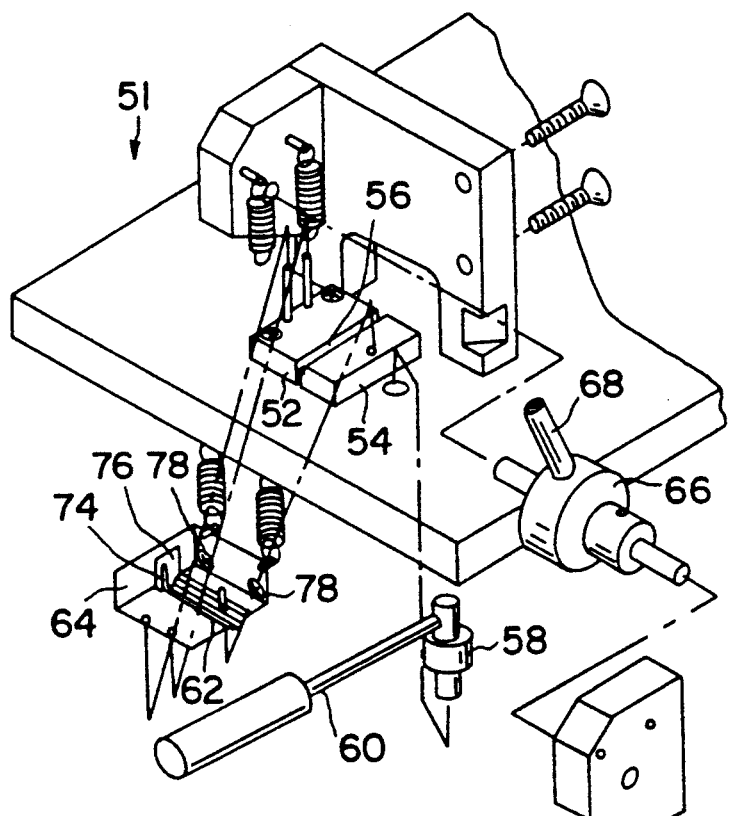
FIG. 12 is an exploded view of the apparatus of FIG. 11.
Figure 13:
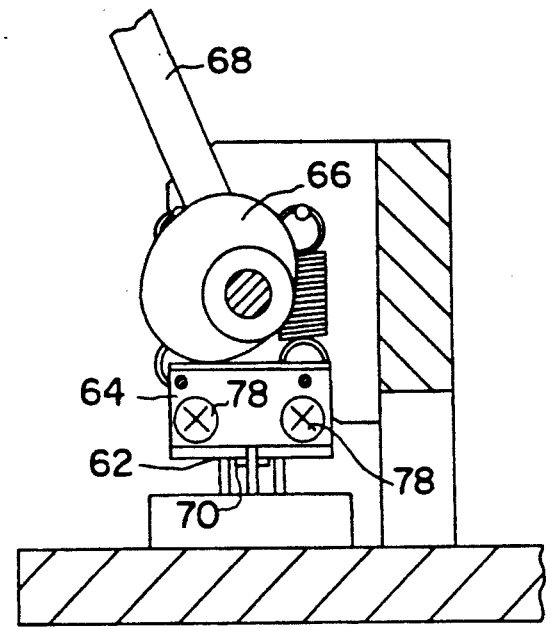
FIGS. 13 and 14 are side elevational views, in cross-section, of the apparatus of FIG. 11, in non-crimping and crimping positions, respectively.
Figure 14:
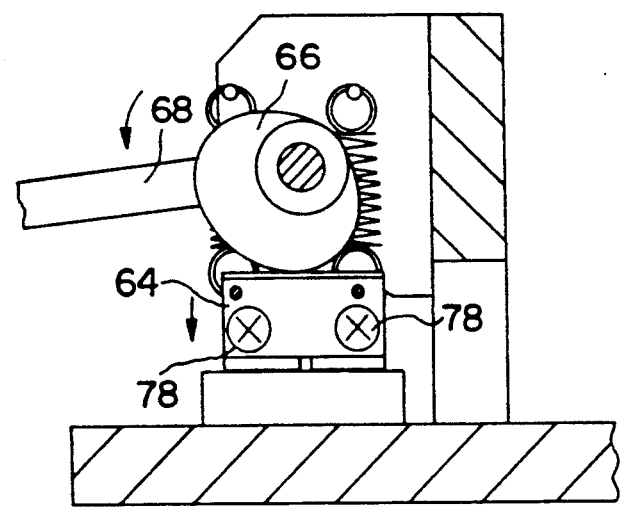
Figure 15:
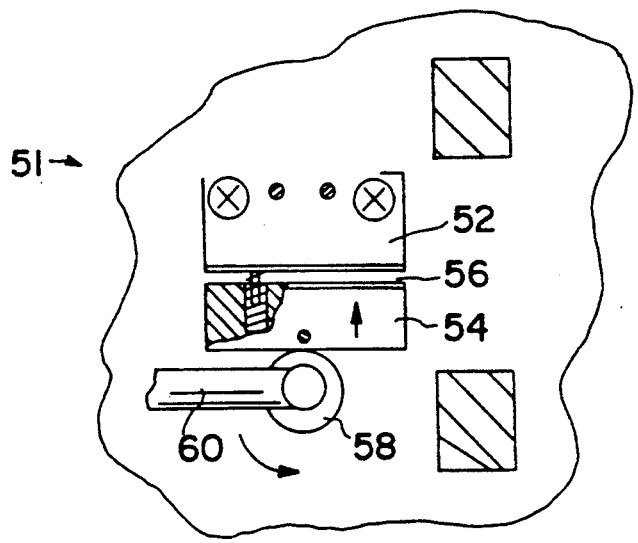
FIG. 15 is a top view in cross-section of the device of FIG. 11, showing the variably-positioned holder for the catheter.

Details of the preferred embodiment are shown in FIGS. 2 and 3 and cross-sections are shown in FIGS. 4A through 4F. In the preferred embodiment, the catheter body 4 is formed of jacketed spring coil, preferably a proximal 20 and distal 22 coil placed end-to-end and spaced apart so that a linking element (here formed of flexible tubes 32) can form the transition region 24 therebetween. (The spring coils are of a flat wire type and are made of a biocompatible material such as stainless steel.) The spring coil provides the catheter with flexibility while providing axial stiffness.

The coils are jacketed with polyethylene 28 and define an inflation lumen 30 which passes through the proximal coil, the transition region, and the distal coil into balloon 6 so that the fluid can be passed through the lumen to inflate the balloon for an angioplasty procedure.

A core wire 26 extends through the proximal coil 20 into the distal coil 22 and is bonded directly to both at points 21. The core wire is also formed of stainless steel and is brazed, welded or soldered to the coil. (Laser welding is preferred.) The bond avoids the necessity of melting or otherwise creating a separate lumen for the core wire and imparts stability and stiffness to the catheter.

The core wire stiffens the catheter in the area where the guidewire runs exterior to the catheter body, provides additional axial support, and also forms a safety wire to anchor the distal coil to the proximal coil. The diameter of the core wire in the preferred embodiment tapers from about 0.016 in. at the proximal end to about 0.010 in. at the transition region to about 0.0025 in. at its distal end, but can vary depending on grade of material.

The transition region 24 is formed in this catheter of a linking element (here flexible tubes 32) which provides a bridge between the two spring coils forming the catheter body. It serves in this catheter to locate the guidewire entry 12 (also referred to as the distal entry or side port entry). The use of a linking element such as that described herein to create a three-part catheter shaft provides great flexibility in manufacturing the catheter; by varying the materials and design of the linking element and the shaft, different catheter characteristics can be obtained. In the preferred embodiment, the linking element is formed from one or more, preferably two, parallel flexible tubes 32 which link the inflation lumens of the two adjacent coils. (In another embodiment described in more detail below, it is formed of a multilumen insert.)

The tubes 32 are formed of a flexible biocompatible material. The material should be heat resistant and will retain its shape during the heating operation. The material used in the preferred embodiment is a polyimide. The advantage of a polyimide is that polyethylene or other materials needed to seal off the remainder of the inflation lumen or anchor the flexible tubes in place will bond to it. Teflon TM can be used but does not bond well without special surface treatment; polyethylene may be used but has a lower melting point and will require the use of a mandrel during manufacture to maintain the patency of the lumen due to its heat sensitivity.

The flexible tubes must also be large enough to provide adequate balloon inflation and deflation times while maintaining a small cross-section. For a catheter with a transition region diameter of about 0.43 in., polyimide tubes having an outer diameter of 0.012 in. and an inner diameter of 0.010 in. are preferred.

The polyimide tubes are anchored in place by a polyethylene plug 34 which also serves to seal the coils' inflation lumen from the exterior of the catheter at the side port entry. The transition zone is preferably about 1.5 cm. in length and the flexible tubes about 2.0 cm. in length.

The inner lumen 10 is formed of a high density polyethylene tube; in the preferred embodiment, it is about 0.017 in. in inner diameter and 0.022 in. in outer diameter. It is located within the catheter body and extends through the balloon to form, at its distal end, the distal end of the catheter, 14. It is anchored in place at its proximal end by polyethylene plug 34; at its distal end, it is sealed to balloon 10 and simultaneously anchored.

The catheter is made by first welding the core wire to the appropriately positioned spring coils. The polyimide tubes are sleeved with polyethylene (which will ultimately form the polyethylene plug) and positioned in the transition zone. The guidewire lumen, containing a mandrel tapered at its underside at the proximal end, is positioned in the transition region also. The tapered mandrel is desirable because it provides a smooth ramp at the side port entry. An alternate approach to the tapered mandrel is to offset the two spring coils slightly during manufacture, and use a standard mandrel.

The polyethylene jacket (which jackets the coil and the transition region) is positioned over the catheter and heat shrunk in place. The transition region is heated to assure that the polyethylene plug has formed and sealed the transition region. The guidewire port is cut using methods known in the art. The balloon and manifold are then attached in a conventional manner.

Other ways of manufacturing are to form the linking element or transition region in advance, preferably by molding a multilumen polyethylene unit or element 44 shown in the catheter of FIGS. 5 and 6a through 6F. This catheter also contains two jacketed spring coils 20 and 22 placed end-to-end and linked by a linking element, here in the form of the molded multilumen element 44. This multilumen linking element has a crescent shaped lumen 46 instead of the flexible polyimide tubes (for more economical use of space), and includes the guidewire lumen 10, although the guidewire lumen 10 may be formed separately from the multilumen insert and bonded to it.

The multilumen element can be molded of polyimide or polyethylene and anchored to the jacketing polyethylene and the spring coils during the heat shrinking operation. Wire (not shown) from the distal end of the proximal coil 20 or the proximal end of the distal coil 22 wound helically about the multilumen transition region may be added as a safety wire. A disadvantage of polyethylene for the multilumen insert is that mandrels have to be placed during manufacture in the lumens during the heating operation so that they do not collapse.

Another version of the catheter is shown in FIGS. 7 and 8A through 8F. This embodiment retains the spring coil 20 and its advantages at the proximal end of the catheter, but uses a multilumen extrusion 47 for the distal portion. The multilumen extrusion can be formed of polyethylene, polyimide or other flexible material, and bonded to the proximal lumen during the heat shrinking operation. The multilumen extrusion is a single bilumen extrusion and contains both the guidewire lumen 10 and a crescent shaped inflation lumen 48 for economical use of space; it is inserted at its proximal end into the proximal coil 20 and anchored in a fashion similar to that described above.

Although the extrusion in this embodiment is generally convenient to manufacture, mandrels are necessary during the heat shrinking operation to keep the lumens open. A disadvantage, of course, is that the distal segment of the catheter lacks the handling characteristics of the spring coil, i.e., axial stiffness with flexibility, and that it is very difficult to bond a core wire to the extrusion, further reducing the stability and axial stiffness of the catheter. This drawback can be overcome, however, by reinforcing the extrusion with a braid or fibers. For example, fibers in an extrudable matrix such as Vectra TM made by Hoechst Celanese might be suitable for this extrusion (and, indeed, the proximal segment of this or the other embodiments of the catheter as well).

In yet another embodiment of the present invention, shown in FIGS. 9 and 10A through 10F, the entire catheter shaft is made of one spring coil 50. The side port entry 12 in the transition region is formed by first connecting adjacent coils together in what will be the transition zone 24. Connecting adjacent coils together helps to hold the spring coil steady during crimping; brazing or another high temperature treatment is preferred over welding because it makes the coils more ductile and therefore more amenable to shaping. Additional strength can be obtained by laser welding each adjacent coil to the core wire as well.

The group of adjacent connected coils in zone 24 are then carefully crimped using a crimping tool such as a machinist's scribe or the specially designed tool of FIGS. 11 through 15. The crimping is controlled to provide a gradual, smooth transition into the spring coil shaft, while retaining the inflation lumen. As shown in FIG. 9, the desired entry angle 71 is about 6 degrees, and the entry can be hand-crimped to provide the desired angle, or a device such as that shown in FIG. 11 can be used to easily create the crimping angle.

To maintain the inflation lumen during crimping, a core wire, (preferably two of about 0.014" in diameter) is placed in the lumen during the crimping. In the preferred embodiment, a hypotube mandrel split lengthwise to form a crescent or U, is inserted during crimping to maintain and shape the inflation lumen.

After crimping, one or more, preferably two, short flexible tubes, specifically polyimide shafts 32 such as those described earlier, are inserted by mandrel into the inflation lumen in the transition zone to transport inflation fluid between the distal and proximal portion of the spring coil shaft. A seal, preferably of a polymer such as polyethylene, or an adhesive such as a cyanoacrylate, a UV-cured adhesive, or an epoxy, is then inserted to seal the polyimide shafts in place and block the remainder of the inflation lumen from fluid flow.

The guidewire lumen itself is then inserted and fixed to the side port entry, and the remainder of the catheter is finished.

In the preferred version of this embodiment of the invention, the spring coil outer diameter is about 0.034 in., the length of crimp is about 0.200 in. (200 mm), and the angle 71 of taper is 6 degrees.

The crimping apparatus 51 illustrated in FIGS. 11 through 15 is a prototype designed to crimp spring coils of various sizes. As shown in particular in FIG. 15, the device includes two blocks 52 and 54 spaced from each other to create a groove 56 therebetween for retaining the coil during crimping. The two blocks are preferably movable with respect to each other, so that the spring coil can be easily put in place, and so that coils of different sizes can be accommodated. An eccentric cam 58 together with an arm 60 attached thereto is included for variably spacing the blocks.

A tongue 62 for crimping the coils is placed in another block 64 mounted above the two spaced blocks. This block, too, is movable with respect to the coil to position the tongue in crimping and non-crimping positions, as shown in particular detail in FIGS. 13 and 14. The positioning means is an eccentric cam 66 with an arm 68 attached to it so that the block can be positioned with the tongue at various depths to provide different amounts of crimp for different coils. The tongue preferably has a lower edge 70 which is tapered lengthwise, preferably at an angle of about 6 degrees, to create the 6-degree entry angle mentioned above.

The tongue is held in a slot 74 in fixture 76 fitted in block 64. The fixture can be removed from the block and the tongue from the slot in the fixture, by removing screws 78, so that a tongue of a different length or a different taper can be inserted into the fixture and block.

In use, a tongue of selected size and taper is placed in fixture 76 and upper block 64 is assembled with the tongue and fixture. Block 54 is positioned with respect to block 52 using arm 60 and the spring coil to be crimped is placed in groove 56. Arm 60 is repositioned to fixedly retain the spring coil. Crimping is completed by using arm 68 to adjust the position of block 64 and tongue 62 to crimp the coil.

From the foregoing detailed description of specific embodiments of the present invention, it should be apparent that a catheter with a side port entry and method for making and using same have been described. Although particular embodiments of the invention have been described herein in some detail, this has been done for the purposes of illustration only and is not intended to be limiting with respect to the scope of the invention. It has been contemplated by the inventors that various changes, alterations, or modifications may be made to the invention as described herein without departing from the spirit and scope of the invention as defined by the appended claims.

What is claimed is:

1. A catheter comprising:
  a spring coil shaft and having an inflation lumen;
  a side port;
  a distal and proximal end;
  a balloon located generally at the distal end of the shaft, the balloon having a distal end and a proximal end; and
  a guidewire lumen extending from the spring coil shaft distal end to the side port, said guidewire lumen adapted to receive a guidewire in a sliding fit, wherein the distal end of the balloon is sealed to the inflation lumen.

2. A catheter according to claim 1 and wherein the shaft is jacketed with polyethylene.

3. A catheter according to claim 1 and wherein the spring coil shaft is formed of two spring coils placed end to end with a transition region therebetween, said transition region formed of a flexible tube, the side port entry located in the transition region, and each spring coil having an inflation lumen.

4. A catheter according to claim 3 and wherein the flexible tube located within the transition region defines an inflation lumen in fluid communication with the inflation lumens of the two coils.

5. A catheter according to claim 4 and wherein two flexible tubes are located within the transition region.

6. A catheter according to claim 3 and wherein a core wire extending through the inflation lumen of the shaft is affixed to the two coils.

7. A catheter according to claim 1 and further comprising a first flexible tube sealed into the spring coil shaft adjacent the side port and said first flexible tube in fluid communication with the inflation lumen in the spring coil shaft.

8. A catheter according to claim 7 and further comprising a second flexible tube sealed into the spring coil shaft parallel to the first tube and the tubes are formed of polyimide, said second flexible tube being in fluid communication with the inflation lumen in the spring coil shaft.

9. A catheter body comprising:
  a distal tubular member having
    a longitudinal distal inflation lumen throughout and
    a longitudinal inner guidewire lumen throughout;
  a proximal tubular member, the proximal tubular member being formed of a jacketed spring coil and having
    a longitudinal proximal inflation lumen throughout; and
  a transition region formed of a flexible tube and having
    at least one flexible transition inflation lumen allowing the distal inflation lumen and the proximal inflation lumen to be in fluid communication, the distal and proximal inflation lumens being placed end to end and the transition region being affixed to the proximal tubular member and to the distal tubular member;
    a side port entry in the transition region from which the guidewire lumen exits to the catheter exterior; and
    a seal surrounding the transition inflation lumen and filling the transition region to seal the side port from the distal inflation lumen and from the proximal inflation lumen.

10. A catheter body comprising:
  a distal tubular member having
    a longitudinal distal inflation lumen throughout and
    a longitudinal inner guidewire lumen throughout;
  a proximal tubular member, the proximal tubular member being formed of a jacketed spring coil and having
    a longitudinal proximal inflation lumen throughout; and
  a transition region formed of a flexible tube and having at least one flexible transition inflation lumen allowing the distal inflation lumen and the proximal inflation lumen to be in fluid communication, the distal and proximal inflation lumens being placed end to end and the transition region being affixed to the proximal tubular member and to the distal tubular member;

a side port entry in the transition region from which the guidewire lumen exits to the catheter exterior; and wherein the transition region includes a second flexible tube.

11. A catheter according to claim 10 and wherein the transition inflation lumen is formed of polyimide.

12. A catheter body comprising:
a distal tubular member having
a longitudinal distal inflation lumen throughout and
a longitudinal inner guidewire lumen throughout;

a proximal tubular member, the proximal tubular member being formed of a jacketed spring coil and having
a longitudinal proximal inflation lumen throughout; and a transition region formed of a flexible tube and having
at least one flexible transition inflation lumen allowing the distal inflation lumen and the proximal inflation lumen to be in fluid communication, the distal and proximal inflation lumens being placed end to end and the transition region being affixed to the proximal tubular member and to the distal tubular member;

a side port entry in the transition region from which the guidewire lumen exits to the catheter exterior; and further comprising a core wire affixed to each of the distal and proximal tubular members.

* * * * *